United States Patent [19]

Hessel et al.

[11] Patent Number: 5,415,665
[45] Date of Patent: May 16, 1995

[54] UMBILICAL CORD CLAMPING, CUTTING, AND BLOOD COLLECTING DEVICE AND METHOD

[75] Inventors: Stephen R. Hessel, Fountain Valley; H. Theodore Young, Lake Forest; Michael Katz, Richmond, all of Calif.

[73] Assignee: Utah Medical Products, Inc., Midvale, Utah

[21] Appl. No.: 9,020

[22] Filed: Jan. 26, 1993

Related U.S. Application Data

[63] Continuation-in-part of Ser. No. 672,535, Mar. 19, 1991, Pat. No. 5,190,556.

[51] Int. Cl.⁶ ............................................. A61B 17/00
[52] U.S. Cl. ..................................... 606/120; 604/4; 128/760; 128/764
[58] Field of Search ............... 606/120; 604/4, 5, 6, 604/22, 35; 128/760, 764, 765

[56] References Cited

U.S. PATENT DOCUMENTS

| | | |
|---|---|---|
| 4,327,746 | 5/1982 | Feaster ................................ 128/764 |
| 4,428,374 | 1/1984 | Auburn ............................ 606/120 X |
| 4,716,886 | 1/1988 | Schulmann et al. ................ 606/120 |
| 4,781,188 | 11/1988 | Collins ................................ 606/120 |
| 4,938,215 | 7/1990 | Schulman et al. .................. 606/120 |
| 4,972,843 | 11/1990 | Brodén ........................... 128/764 X |
| 4,976,271 | 12/1990 | Blair .................................... 128/764 |
| 5,009,657 | 4/1991 | Cotey et al. ........................ 606/120 |
| 5,190,556 | 3/1993 | Hessel ................................ 606/120 |

Primary Examiner—Peter A. Aschenbrenner
Attorney, Agent, or Firm—Madson & Metcalf

[57] ABSTRACT

There is disclosed herein a device for clamping and cutting an umbilical cord so as to enable blood samples from the umbilical cord to be collected and/or tested. The device provides for the clamping of a severed end of an umbilical cord and the automatic ejection of that clamped end. The device also provides for the cutting of an umbilical cord without using excessive force regardless of the size of the umbilical cord. Additionally, the device provides for the valved use of vacuum tubes to collect umbilical cord blood samples. Furthermore, the device enables the measurement of blood values at the moment of cutting the umbilical cord. Finally, the device also provides for the protection of users and others from exposure to sharps and blood.

7 Claims, 19 Drawing Sheets

UMBILICAL CORD CLAMPING, CUTTING, AND BLOOD COLLECTING DEVICE AND METHOD

INTRODUCTION

This application is a continuation-in-part of application Ser. No. 672,535 entitled "Cord Cutter Sampler" filed Mar. 19, 1991, now U.S. Pat. No. 5,190,556.

The present invention relates to medical devices for clamping, cutting, and sampling vessels, in particular umbilical cords.

BACKGROUND

There are many difficulties encountered by physicians and nurses in the process of cutting an umbilical cord shortly after the moment of birth. These difficulties cannot be overcome easily by current technology.

Difficulties arise due to the fact that at the moment of birth there is a great deal of fluid present, including blood and amniotic fluid from the mother, making the physician's gloved hands slippery. The procedure of clamping and cutting an umbilical cord first calls for the placement of a small first clamp close to the newborn to stop the flow of blood in the cord and to clamp off what will become a first severed end of the cord (the end of the cord connected to the infant). The combination of the small clamp size and the fluid on the physician's gloved hands creates difficulty in applying the first clamp. In some cases the physician cannot adequately close the clamp around the cord forcing the temporary use of a metal hemostat in its place. Replacing the hemostat with a clamp requires placing the clamp on the cord and re-cutting the cord stump. This procedure is often done as late as the infant's arrival in the nursery.

Next, a second clamp must be placed by the physician sufficiently distal to the first to allow a cut to be made between the first and second clamps and to clamp off what will become a second severed end of the cord (the end of the cord connected to the placenta). Generally, this procedure is also made by the deliverer while balancing the neonate in one arm. This procedure often presents the same difficulties as described above.

Additional difficulties are presented because the cord is engorged with blood at birth and when the cord is severed blood commonly spurts from the incision spattering the medical team with droplets. As a consequence, it is routine practice for the medical staff to wear protective eye wear during the process for the purpose of protecting them from exposure to blood. However, sometimes these protective elements dangerously block the view of the wearer (who may be a physician).

Routinely samples of blood from the cord are collected for chemical and biological assay. Such assays may include testing to determine whether the newborn is subject to possible genetically transmitted diseases. Currently two alternative methods are used to collect cord blood samples. These methods include draining the blood from the cord segment directly into an open vial or extracting the blood directly from the cord by using a syringe and needle.

The draining method requires holding an open ended sample vial below the second severed end of the cord (the end connected to the placenta) while releasing the clamp from that severed end and directing the blood flow from that severed end into the sample vial. In most cases the cord segment must be hand "milked" by squeezing the cord such that the blood in the segment flows toward the vial. This "milking" action causes the flow of many contaminants in addition to the desired blood into the vial. Such contaminants include the mother's vaginal blood, amniotic fluids and Wharton's gel, all of which may affect the testing of the cord blood sample. As the complexity and sensitivity of the genetic tests increase, the absence of contamination in the sample becomes more important.

The extracting method requires using a syringe and needle to remove the blood directly from the cord. The needle is used to puncture the cord and the syringe is used to collect a blood sample. Care must be taken to prevent inadvertent needle sticks (which can lead to blood exposure). The contents of the syringe must then be transferred into appropriate vials. This transfer requires further steps of manipulating needles and syringes which create additional risks of blood exposure.

In addition, both of these blood collection methods leave contamination from blood on the external portions of the vials making it difficult to apply or retrieve patient labels and increasing exposure to blood. Thus, there are many problems associated with the current methods of collecting blood samples from umbilical cords.

A device has been designed, fabricated and tested which provides a much improved method of collecting samples of blood from an umbilical cord. The purpose of this device is to provide: (1) simple one handed clamping of umbilical cords at birth, regardless of size; (2) cutting umbilical cords; and (3) automatically delivering adequate samples of uncontaminated cord blood suitable for current laboratory analysis to protected containers with little or no exposure to inadvertent blood splash or to sharp objects.

Embodiments of the device have been assembled, sterilized, and tested by physicians in cases of both vaginal and caesarian births. The devices have effectively collected samples of cord blood. Duplicate samples of blood taken by conventional methods were tested as a control to assure the integrity of the device. The clinical testing was performed under controlled conditions during the last quarter of 1991.

DESCRIPTION OF THE PREFERRED EMBODIMENT

Figure 1:
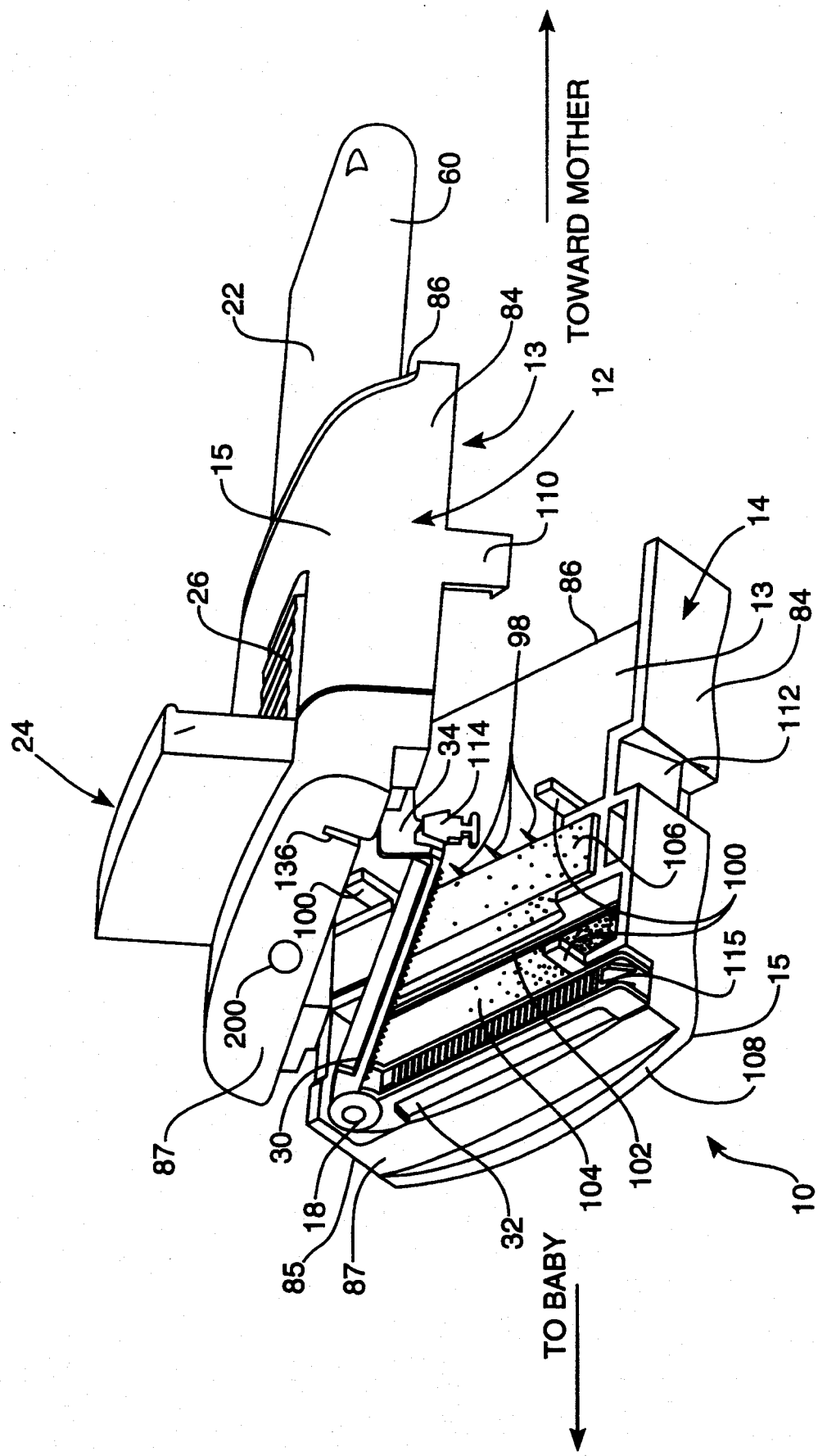
FIG. 1 is a perspective view of the preferred embodiment of an umbilical cord clamping, cutting, and blood collecting device in an open position.
Figure 2:
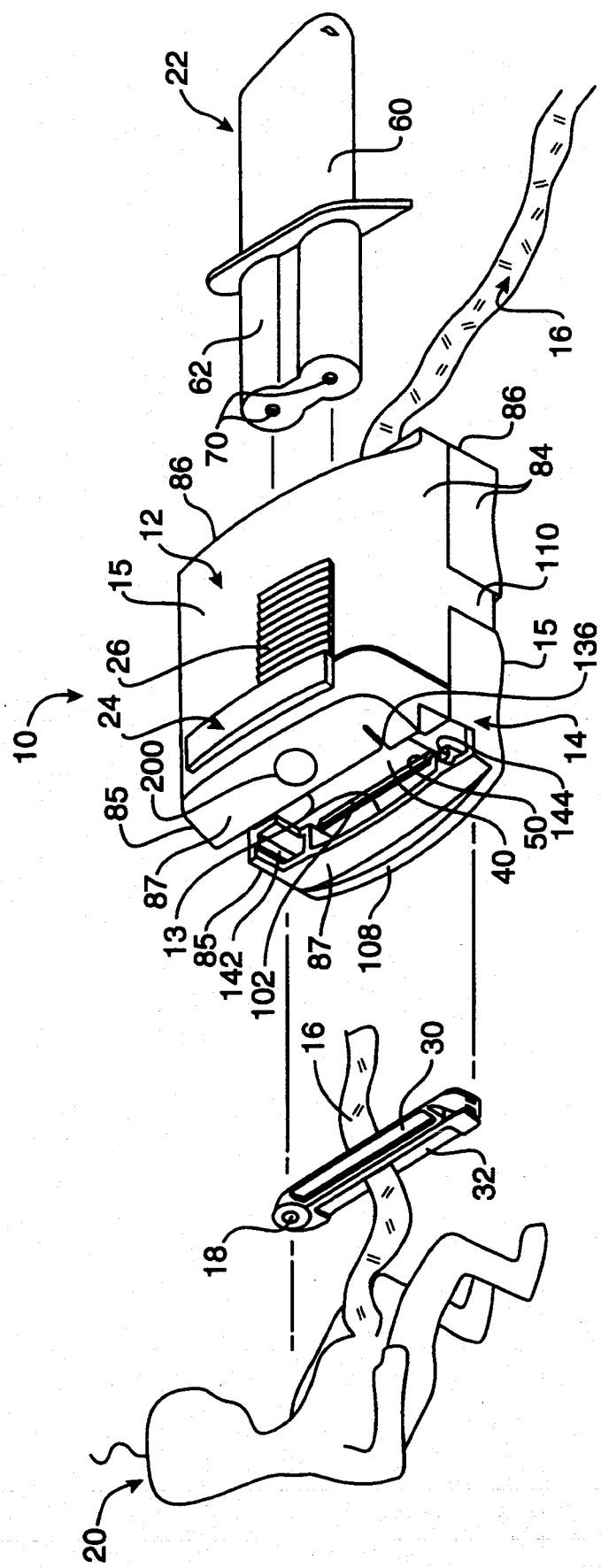
FIG. 2 is a perspective view of the device of FIG. 1 in a closed position.
Figure 3:
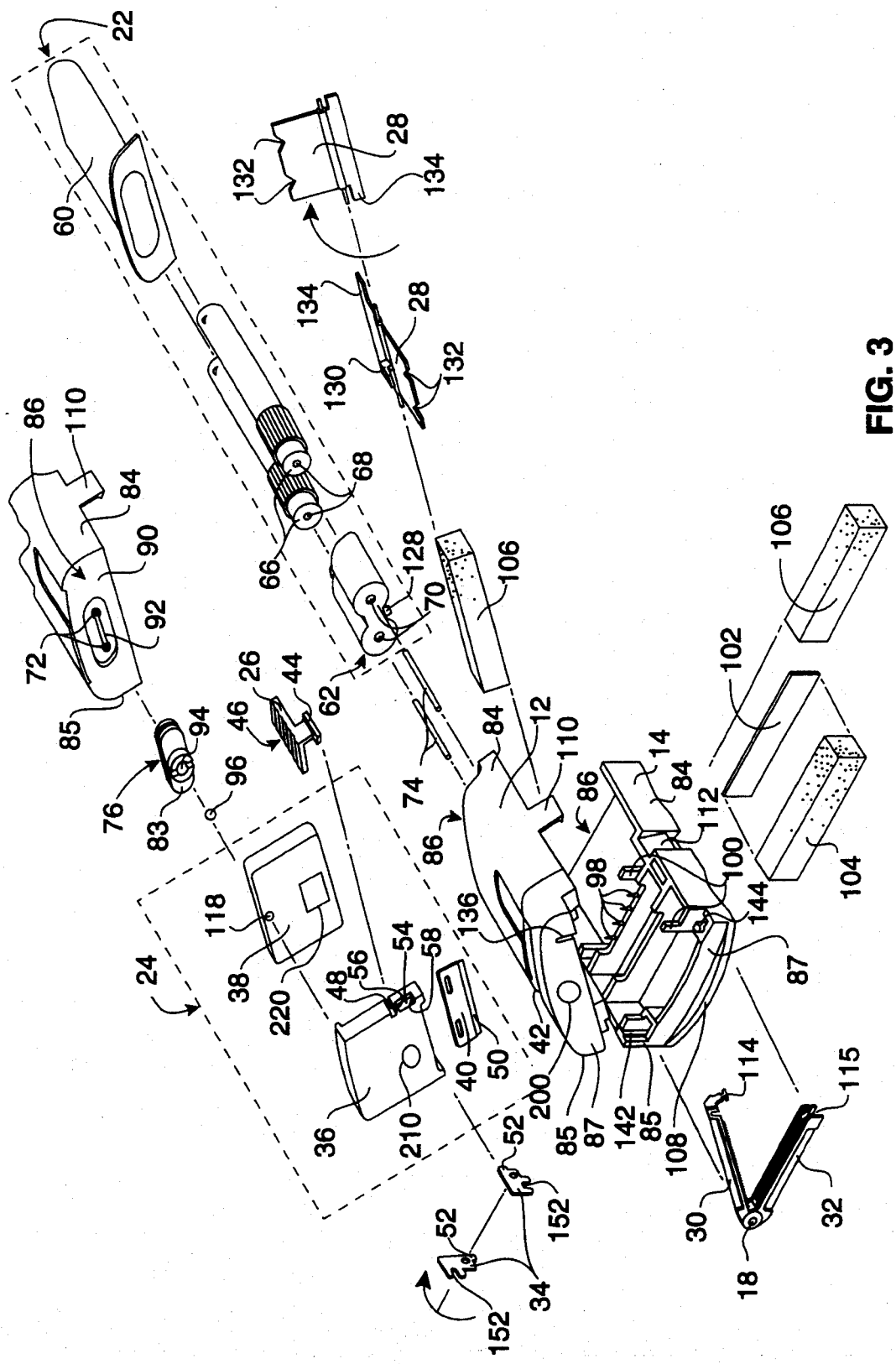
FIG. 3 is an exploded view of the device of FIG. 1 showing its various components.

Turning now to the drawings, and FIGS. 1 and 2 in particular, a preferred embodiment of the umbilical cord clamping, cutting, and blood collecting device 10 comprises a holding mechanism fabricated as a "clamshell" housing defined by a first housing 12 and a second housing 14 each having an inner surface 13 and an outer surface 15 (FIGS. 1-3). As shown in FIGS. 1-3, the first and second housings 12 and 14 also include a front side 84, a back side 85, a right side 86, and a left side 87. The housings 12 and 14 are preferably made from injection molded plastic. The housings 12 and 14 are attached to each other by a simple and conventional hinge 140 (FIGS. 5A, 5B, 7A, 7B, and 10B) and hinge pin (not shown) arrangement along their respective back sides 85 to thereby comprise a clamshell housing. A removable umbilical cord clamp 18 is attached between the housings 12 and 14 at their respective left sides 87 (FIGS. 1 and 2). The first housing 12 includes a blood collection apparatus 22 attached to its right side 86 and a surgical cutting apparatus 24 which is held in place by a safety lock 26 (FIGS. 1 and 2).

Before proceeding with a detailed description of the structure of the device 10, a general discussion of its operation will be helpful. There are basically four steps in using the device 10. FIG. 1 shows the device 10 in a ready to use state. FIG. 2 shows the device 10 after it has been employed; namely, the device 10 is fastened around an umbilical cord 16 of a baby 20 (FIG. 2) so the inner surfaces 13 are in contact with the umbilical cord 16. Comparing FIGS. 1 and 2, the operation of the device 10 comprises the steps of:

(1) positioning the first and second housings 12 and 14 of the device 10 around an umbilical cord 16 so the clamp 18 is positioned toward the baby 20;

(2) closing the first and second housings 12 and 14 around the umbilical cord to clamp the clamp 18 onto the umbilical cord 16 to thereby stop the flow of blood through the cord 16;

(3) positioning the safety lock 26 to release the cutting apparatus 24; and (4) manipulating the cutting apparatus 24 by forcing it downward to thereby sever the umbilical cord 16 and release the clamp 18 (and baby 20).

Upon cutting the umbilical cord 16, the clamp 18 automatically detaches from the housings 12 and 14 and remains clamped to the part of the cord 16 which is attached to the infant 20 (FIG. 2). Immediately, upon severing the cord 16, the blood collection apparatus 22 begins to collect samples of cord blood (the dynamics of this process are described below and demonstrated in FIGS. 8A-8H). At any time after severing the cord 16, the blood collection apparatus 22 can be removed from the device 10 and the collected blood samples can be analyzed or tested. As described below, when the blood collection apparatus 22 is removed from the device 10, the cord 16 is further automatically clamped by a protector 28 (far right side of FIG. 3). Further clamping of the cord 16 by the protector 28 prevents blood from flowing from the part of the cord 16 which is attached to the placenta (not shown).

Thus, a simple four step method replaces the complicated, dangerous, and time consuming current procedure of placing a first clamp on an umbilical cord, placing a second clamp on the cord, cutting the cord between the clamps, removing the second clamp, placing a vial below the end of the cord which is not clamped, draining and milking the cord to collect the blood therein, and reapplying the clamp to the cord.

The device 10 is primarily constructed of inexpensive injection molded plastic components. It can be manufactured at low costs and can, therefore, be economically discarded after use to thereby preclude the possibility of transmitting diseases through re-use.

Figure 9:
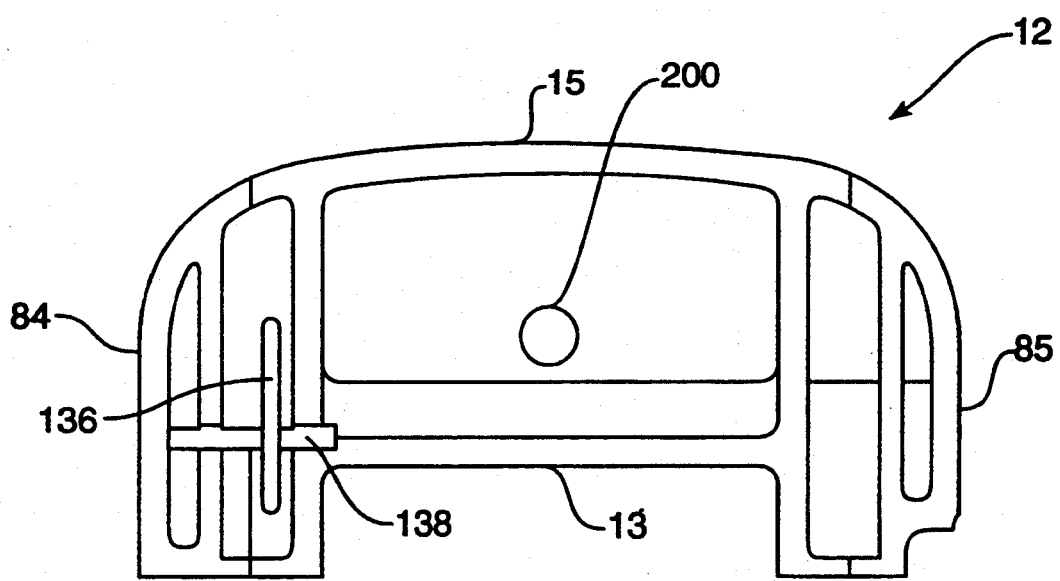
FIG. 9 is a cross-sectional view of the first housing showing the rocker slot and pin slot.

A preferred embodiment of the device 10 is shown in the drawings. As noted above, the device 10 includes a plastic umbilical clamp 18 attached to the housings 12 and 14 at the left sides 87 (FIGS. 1-3). The clamp 18 is preferably made from injection molded plastic. The clamp 18 includes a top arm 30 and a bottom arm 32 (FIGS. 1-3 and 11A-E). The top and bottom arms 30 and 32 hingedly snap together via a hook 148 (FIGS. 11D-E) and axle 150 (FIGS. 11A-B) arrangement to form the clamp 18 (FIGS. 1-3). The top arm 30 of the clamp 18 is fixed onto the first housing 12 (FIG. 1) by means of a rocker 34 (FIGS. 1 and 3). The rocker 34 is rotatably attached to the first housing 12 in a rocker slot 136 (FIGS. 1-3, and 9) in the first housing 12 by means of a pin (not shown) which rests in a pin slot 138 (FIG. 9) in the first housing 12. The rocker 34 may rotate about the pin (not shown). The rocker 34 includes an indentation 152 (FIG. 3) which fits around and holds the top arm 30 of the clamp 18. The rocker 34 is preferably made from stainless steel.

Figure 10A:
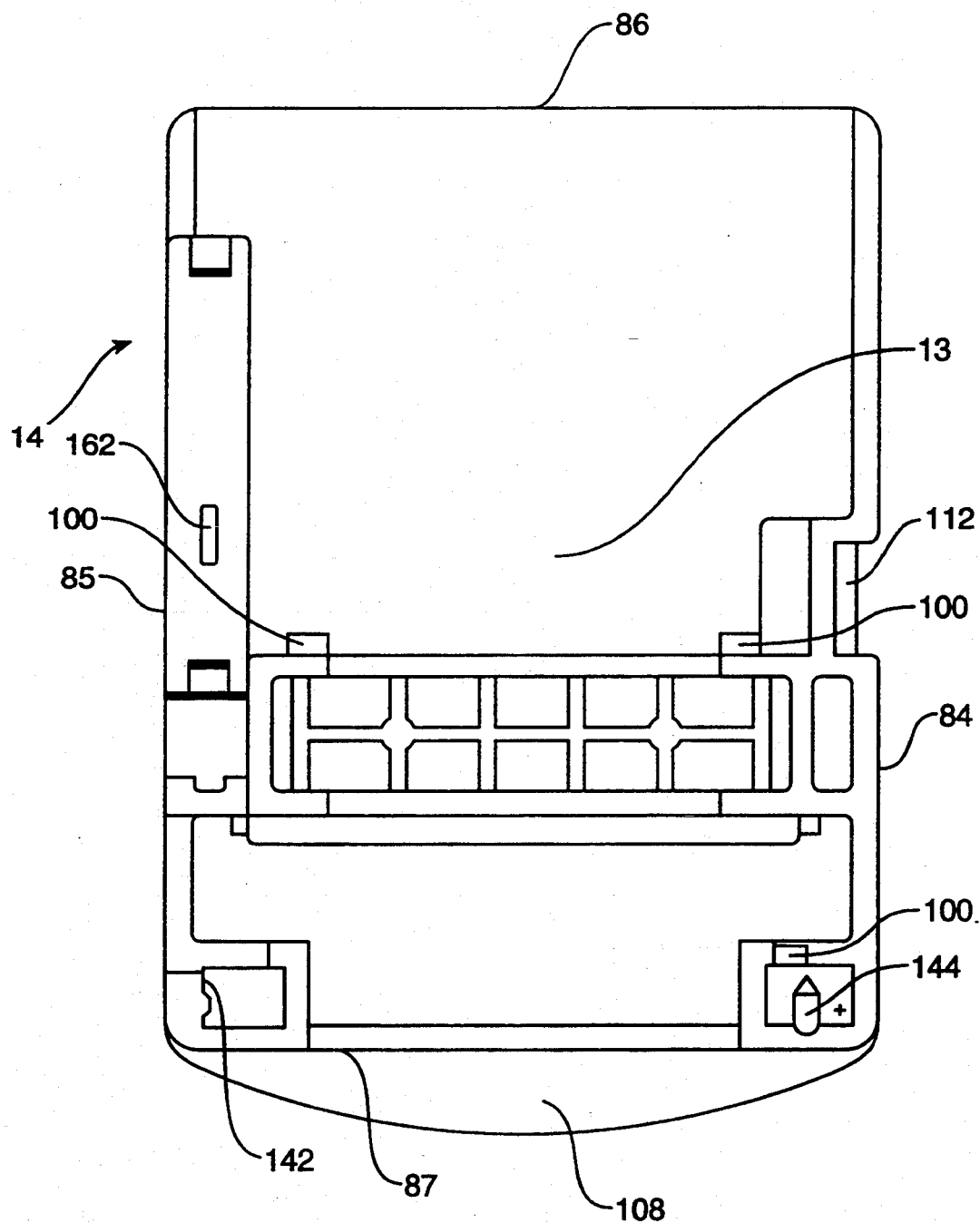
FIG. 10A is a plan view of the second housing.
Figure 10B:
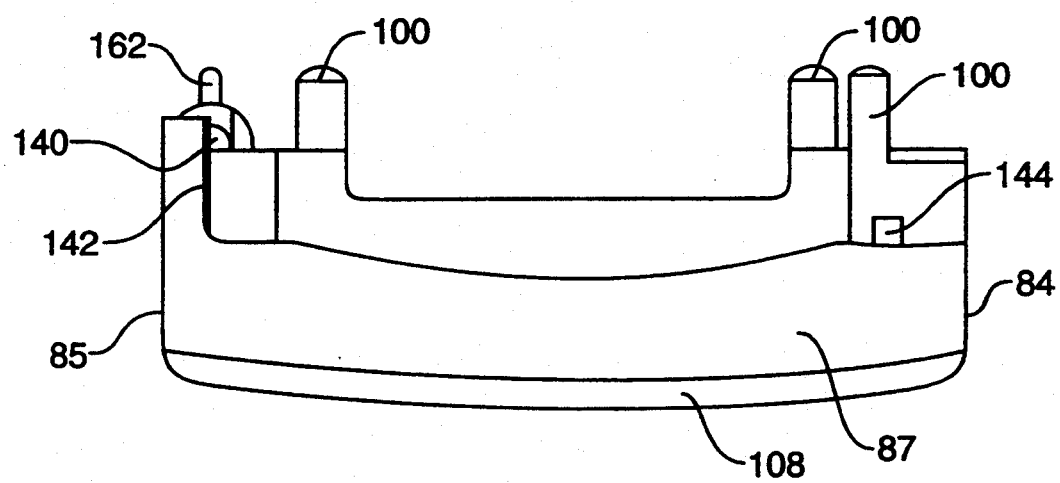
FIG. 10B is a left elevation of the second housing.
Figure 11A:
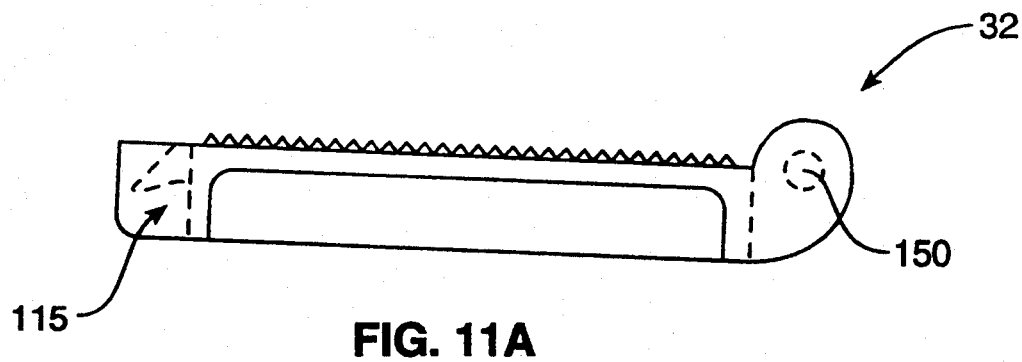
FIG. 11A is a side elevation of the bottom arm of the clamp.
Figure 11B:
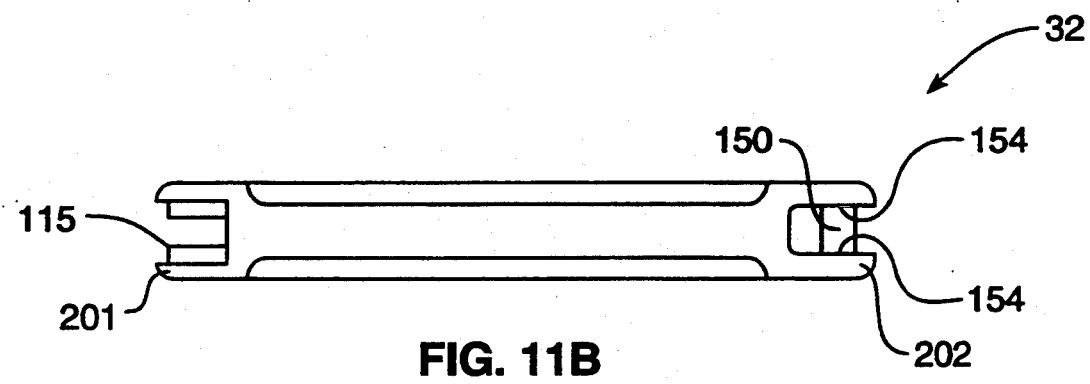
FIG. 11B is a bottom elevation of the bottom arm of the clamp.

The bottom arm 32 of the clamp 18 is attached to the second housing 14 (FIG. 1). As shown in FIGS. 2, 3, and 10A-B, the second housing 14 includes a clamp slot 142 near the back wall 85 and a clamp bump 144 near the front wall 84. As shown in FIGS. 11A and 11B, the bottom arm 32 of the clamp 18 includes fingers 201 and 202. The clamp bump 144 couples to the finger 201 and the clamp slot 142 couples to the finger 202. These couplings allow the bottom arm 32 of the clamp 18 to snap onto the second housing 14.

Figure 11C:
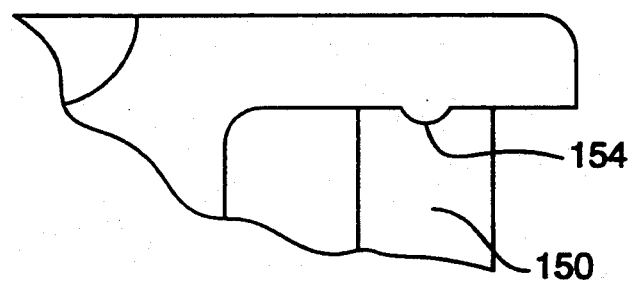
FIG. 11C is an enlarged view of a portion of the bottom arm of the clamp from FIG. 11B.
Figure 11D:
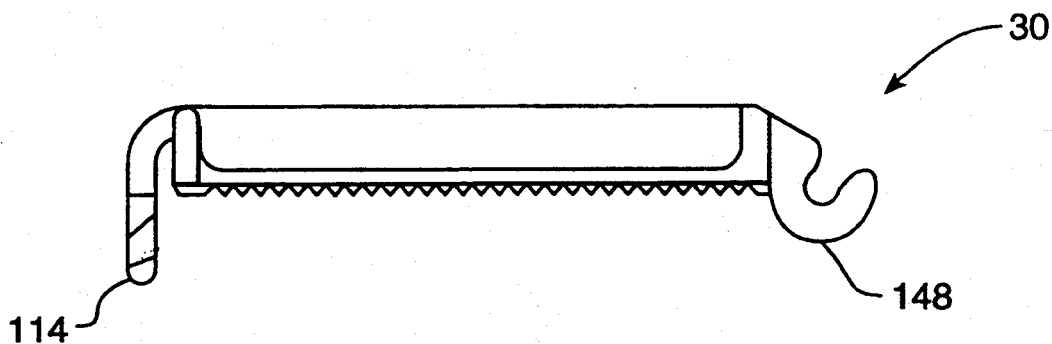
FIG. 11D is a side elevation of the top arm of the clamp.
Figure 11E:
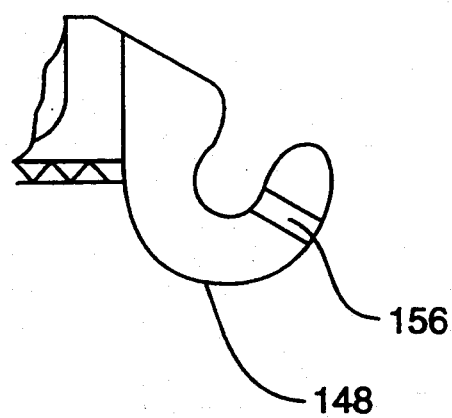
FIG. 11E is an enlarged view of a portion of the top arm of the clamp from FIG. 11C.

The clamp 18 and the device 10 are held open to an angle of approximately sixty degrees by two sets of detents whereby the device 10 is ready for use (as shown in FIG. 1). One set of detents is located on the clamp 18 and the other set of detents is located on the first and second housings 12 and 14. As shown in FIGS. 11B and 11C, the bottom arm 32 of the clamp 18 includes a set of detent bumps 154 near the axle 150. In addition, as shown in FIG. 11E, the top arm 30 of the clamp 18 includes a detent slot 156 on the hook 148 (an identical slot, not shown, is on the opposite side of the hook 148). When the clamp 18 is assembled (i.e. when the clamp hook 148 engages the clamp axle 150), the detent bumps 154 may engage the detent slots 156. When the bumps 154 are caught in the slots 156, the clamp 18 is held open to an angle of approximately sixty degrees.

Figure 5A:
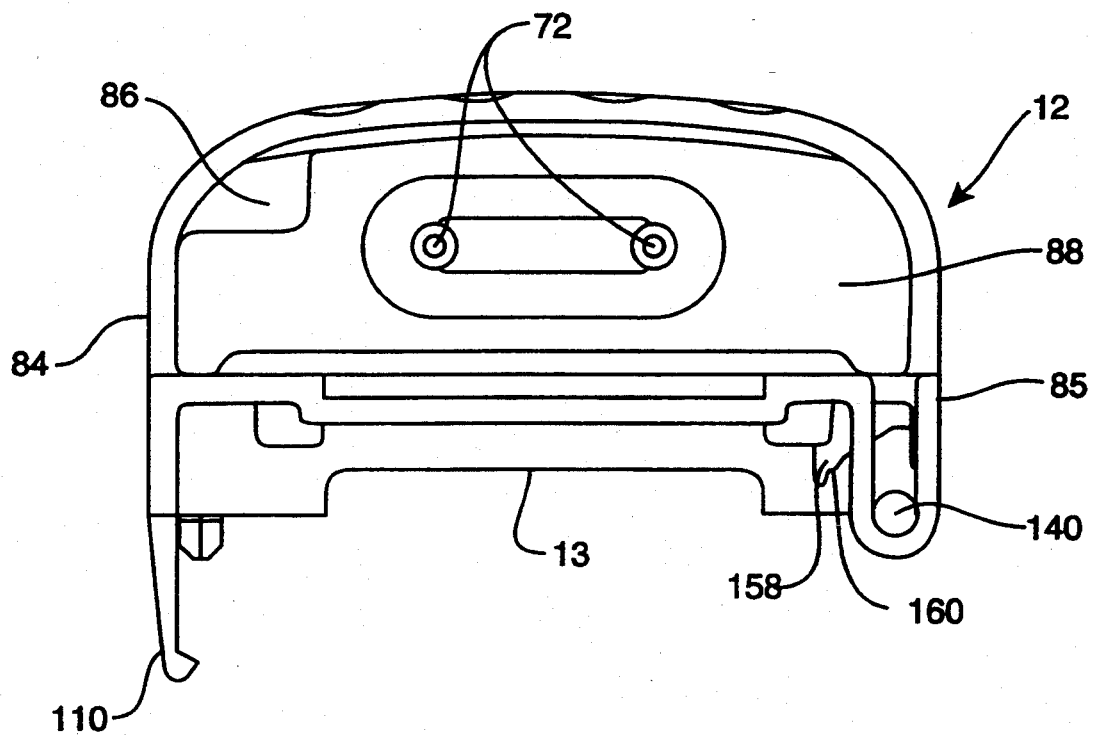
FIG. 5A is a front view of the right wall of the first housing.

In addition, as shown in FIG. 5A, the first housing 12 comprises a detent shelf 158 near the back wall 85 which includes an indentation 160. Furthermore, as shown in FIGS. 10A-B, the second housing 14 comprises a detent tab 162 near the back wall 85. When the housings 12 and 14 are assembled together to form the device 10, the detent tab 162 on the second housing 14 engages the detent shelf 158 and indentation 160 of the first housing 12. When the tab 162 is caught in the indentation 160, the first and second housings 12 and 14 are held open to an angle of approximately sixty degrees.

Figure 4A:
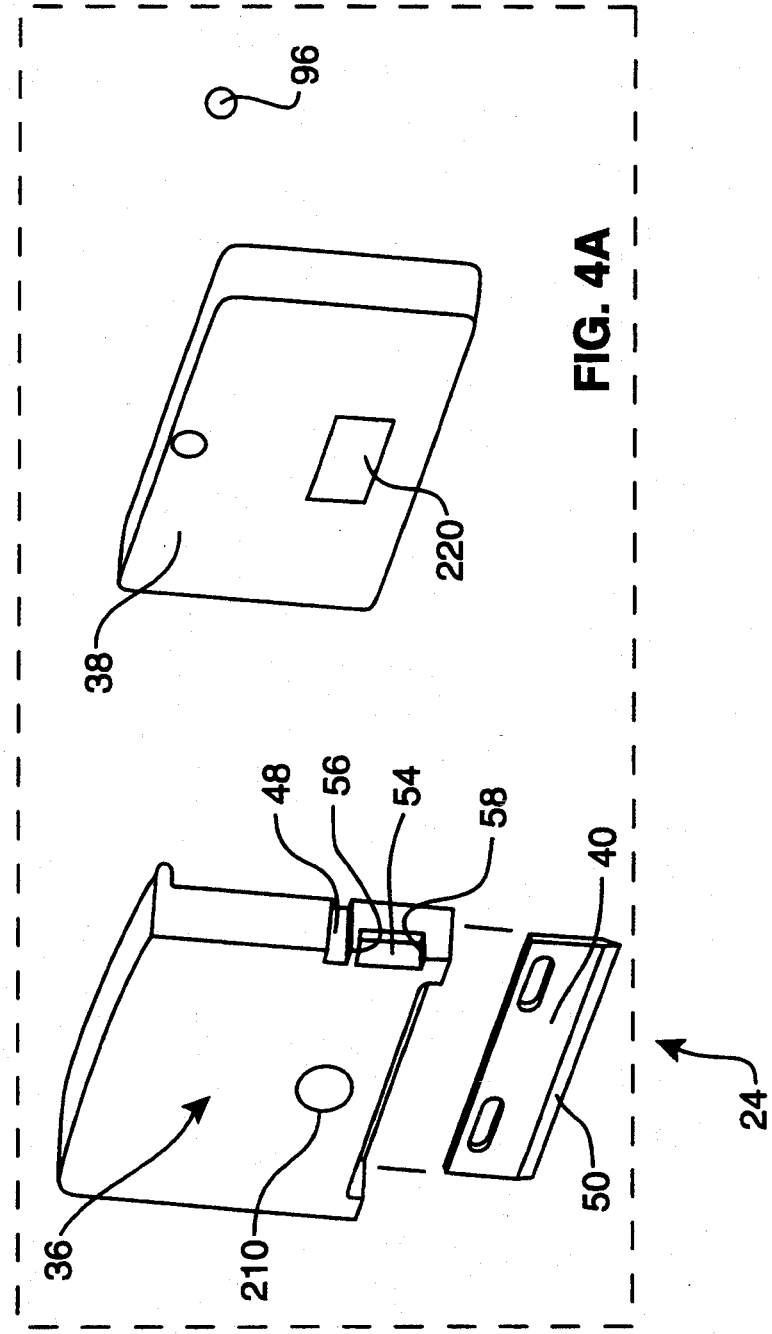
FIG. 4A is an exploded front view of the cutting apparatus of the device of FIG. 1.
Figure 4B:
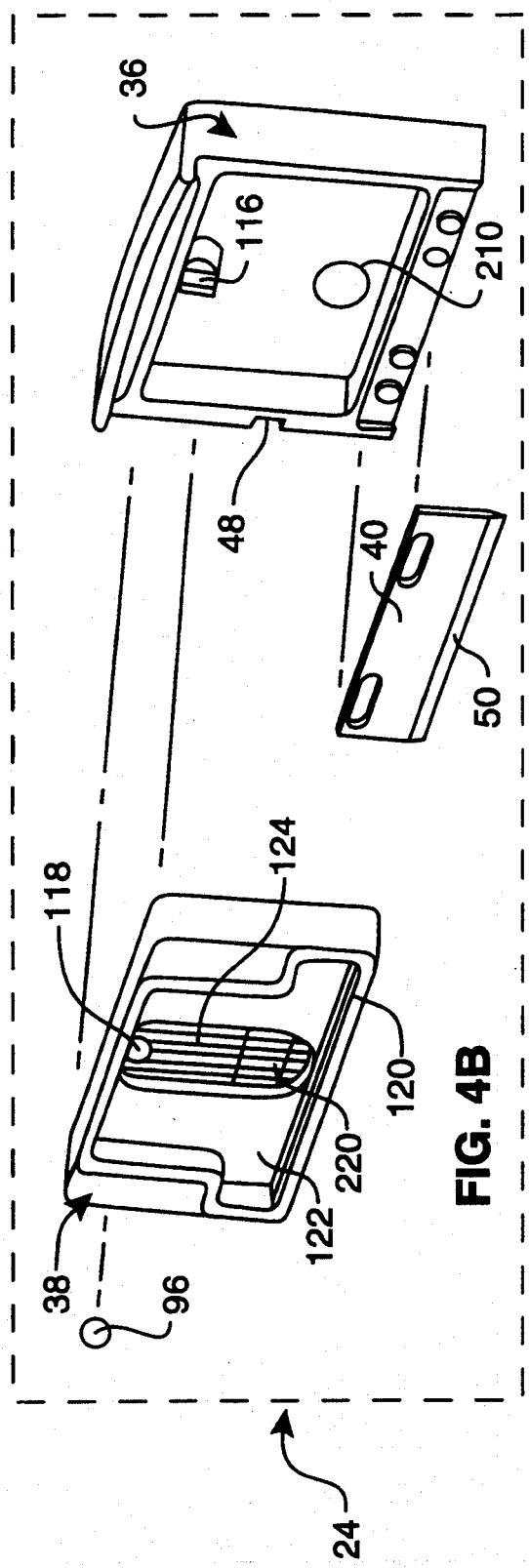
FIG. 4B is an exploded back view of the cutting apparatus of the device of FIG. 1.

As noted above, the device 10 includes a surgical cutting apparatus 24 attached to the first housing 12 (FIGS. 1-3). As shown in FIGS. 3, 4A, and 4B, the cutting apparatus 24 comprises three main components: a slide 36, a gasket 38 which is attached to the slide 36, and a blade 40 which is also attached to the slide 36. The cutting apparatus 24 is positioned in a slot 42 formed in the first housing 12 (FIG. 3) and extends above the outer surface 15 of the first housing 12 (note FIG. 1). The cutting apparatus 24 is prevented from moving downward through the slot 42 by a safety lock 26 which is also attached to the first housing 12 (FIGS. 1-3). The safety lock 26 has an integrally molded locking tip 44 and a finger grip 46 (FIG. 3). The locking tip 44 fits into a lock notch 48 (which is molded on the slide 36 (FIGS. 3, 4A, and 4B)) when the slide 36 is in an up or open position (as in FIG. 1) to thereby hold the slide 36 and, therefore, the cutting apparatus 24 in an up position and prevent the cutting apparatus 24 from moving downward through the slot 42. However, when the locking tip 44 is removed from the lock notch 48, the slide 36 and, therefore, the cutting apparatus 24 are free to be shifted from an up position (FIG. 1) through the slot 42 to a down or cutting position (FIG. 2).

The surgical cutting apparatus 24 includes a blade 40 which has a cutting edge 50 (FIGS. 3, 4A, and 4B). The blade 40 is mounted onto the slide 36 with the cutting edge 50 extending beyond the slide 36 but is recessed in the slot 42 of the first housing 12 when the cutting apparatus 24 is in an up position (whereby the safety lock 26 may be engaged) so that the lower cutting edge 50 of the blade 36 is not exposed when the device is open (FIG. 1). This feature reduces or minimizes the danger of exposure of the cutting edge 50 when the device 10 is in an open position (as in FIG. 1). The cutting edge 50 of the blade 40 severs the umbilical cord 16 when the cutting apparatus 24 is placed in a down or cutting position (FIG. 2).

As described above, a rocker 34 holds the top arm 30 of the clamp 18 onto the first housing 12 (FIG. 1). The rocker 34 includes a back foot 52 (FIG. 3). The back foot 52 of the rocker 34 engages a shelf slot 54 (which is molded on the slide 36 (FIGS. 3 and 4A)) when the slide 36 is in an up position (as in FIG. 1). The shelf slot 54 includes a ceiling 56 and a floor 58 (FIG. 4A) which limit the movement of the back foot 52. When the slide 36 is locked in an up position the back foot 52 is caught in the shelf slot 54 which prevents the back foot 52 from moving and, therefore, prevents the rocker 34 from rotating. As explained later, the rotation of the rocker 34 is important in assisting the release of the clamp 18 from the first and second housings 12 and 14.

As shown in FIG. 3, the blood collection apparatus 22 comprises three main components: a protective sheath 60, a sheath cap 62, and a set of blood collection tubes 64 (which include rubber stoppers 66). The protective sheath 60 snaps over the blood collection tubes 64 and locks to the sheath cap 62 to thereby enclose and protect the blood collection tubes 64 and rubber stoppers 66 (FIG. 2). The rubber stoppers 66 include apertures 68 (FIG. 3) which provide access to the blood collection tubes 64. In addition, the sheath cap 62 includes openings 70 (FIGS. 2 and 3) which provide access to the apertures 68 in the rubber stoppers 66 of the blood collection tubes 64.

Figure 5B:
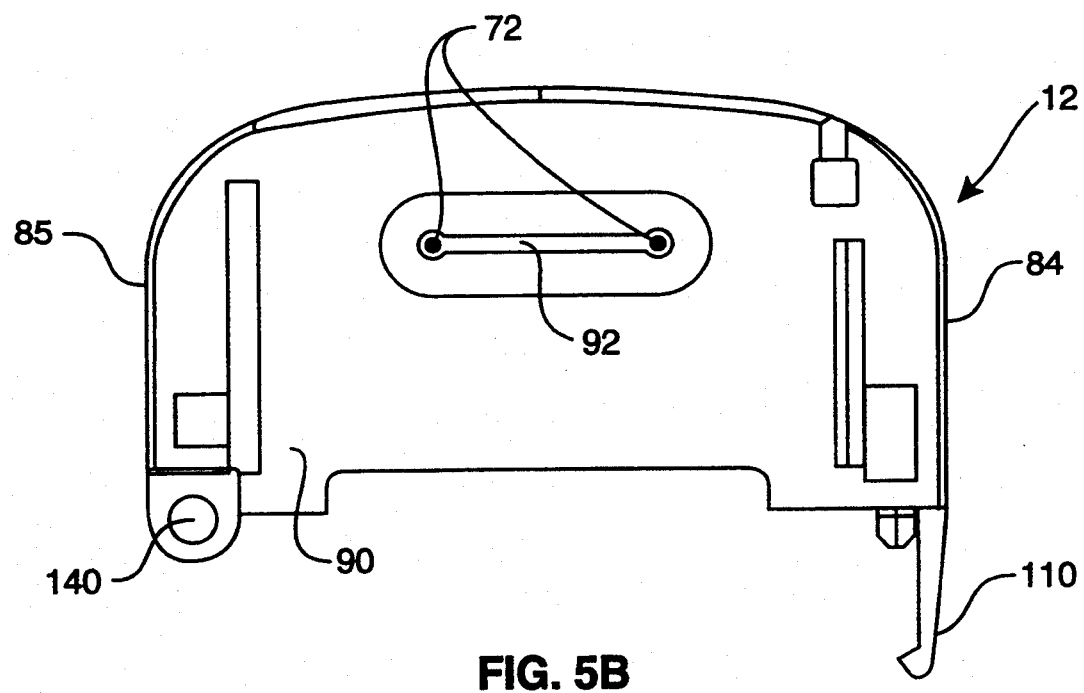
FIG. 5B is a rear view of the right wall of the first housing.

Turning to FIGS. 3, 5A and 5B, the first housing 12 includes a right wall 86 which includes an outer face 88 (FIG. 5A) and an inner face 90 (FIG. 5B). As shown in FIGS. 5A and 5B, the right wall 86 includes communicating holes 72 which extend through the inner and outer faces 90 and 88 and are coupled to each other by a molded channel 92 on the inner face 90 (FIG. 5B). As shown in FIG. 3, needles 74 are mounted in the communicating holes 72 and pass through the openings 70 in the sheath cap 62 and through the apertures 68 in the rubber stoppers 66 to thereby provide a passageway through which a vacuum within the blood collection tubes 64 may communicate to the communicating holes 72 and molded channel 92 of the first housing 12 (see FIG. 3).

Figure 6A:
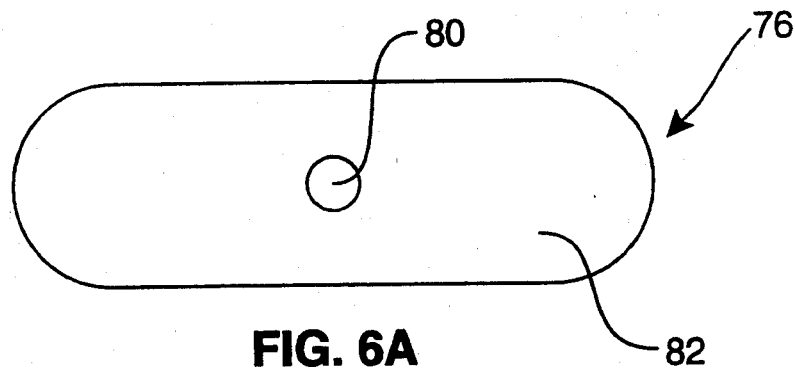
FIG. 6A is a plan view of the right face of the manifold.
Figure 6B:
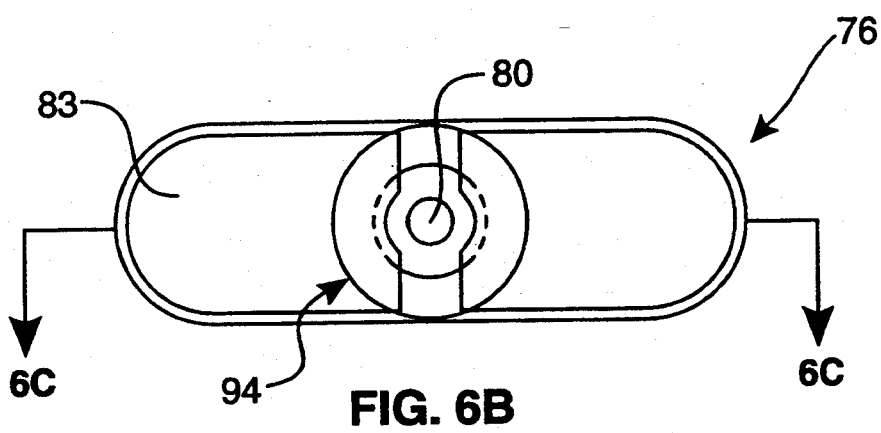
FIG. 6B is a plan view of the left face of the manifold.
Figure 6C:
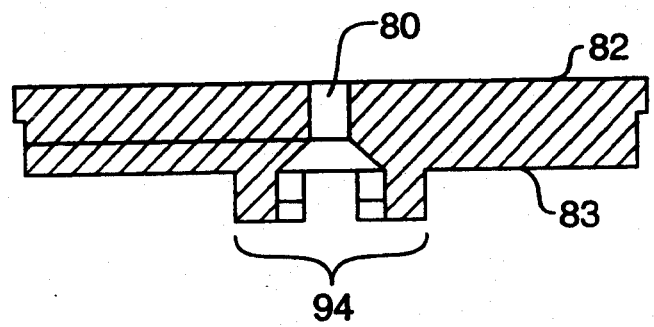
FIG. 6C is a cross section of the manifold taken along line 6C—6C in FIG. 6B.
Figure 7A:
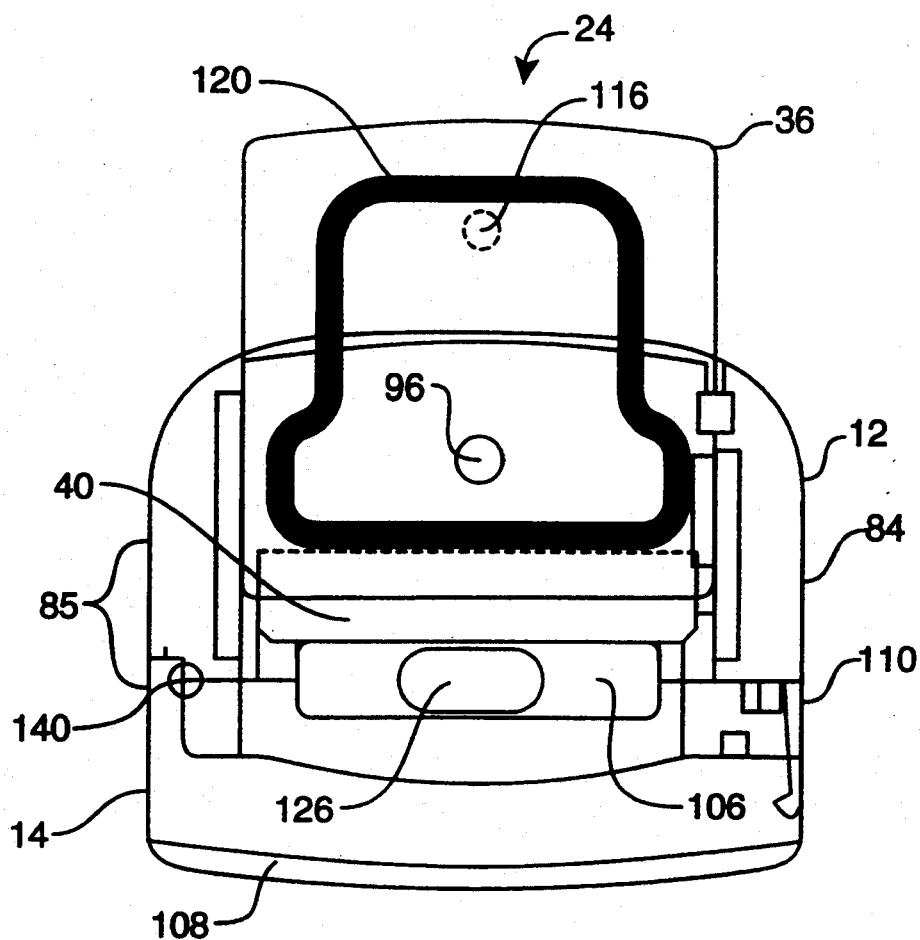
FIG. 7A is a left elevation of the device showing the sealing mechanism and cutting mechanism in phantom before the cutting apparatus has been engaged.
Figure 7B:
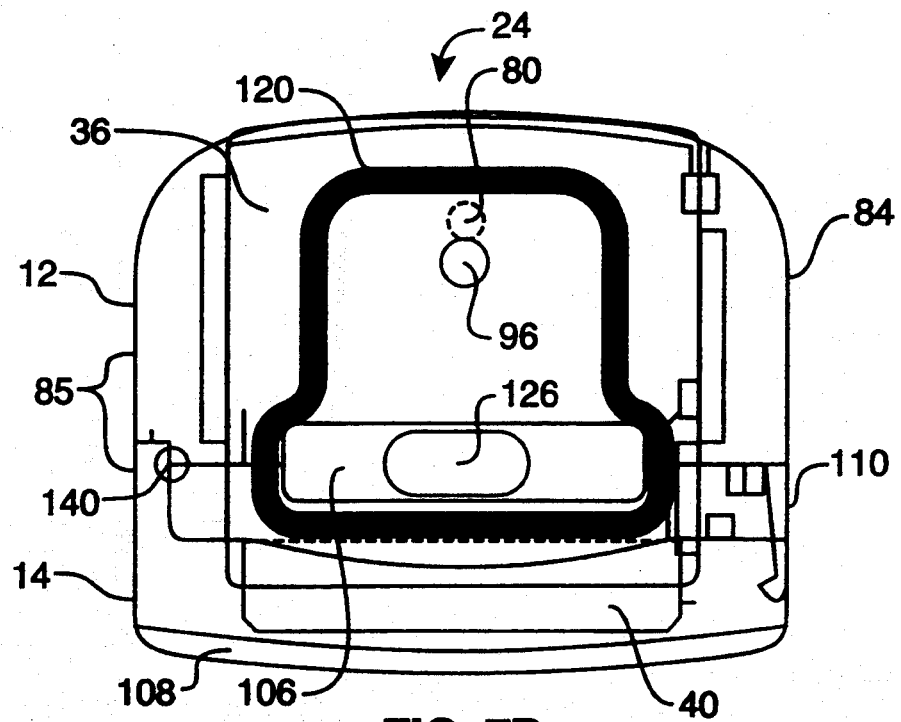
FIG. 7B is a left elevation of the device showing the sealing mechanism and cutting mechanism in phantom after the cutting apparatus has been engaged.
Figure 7C:
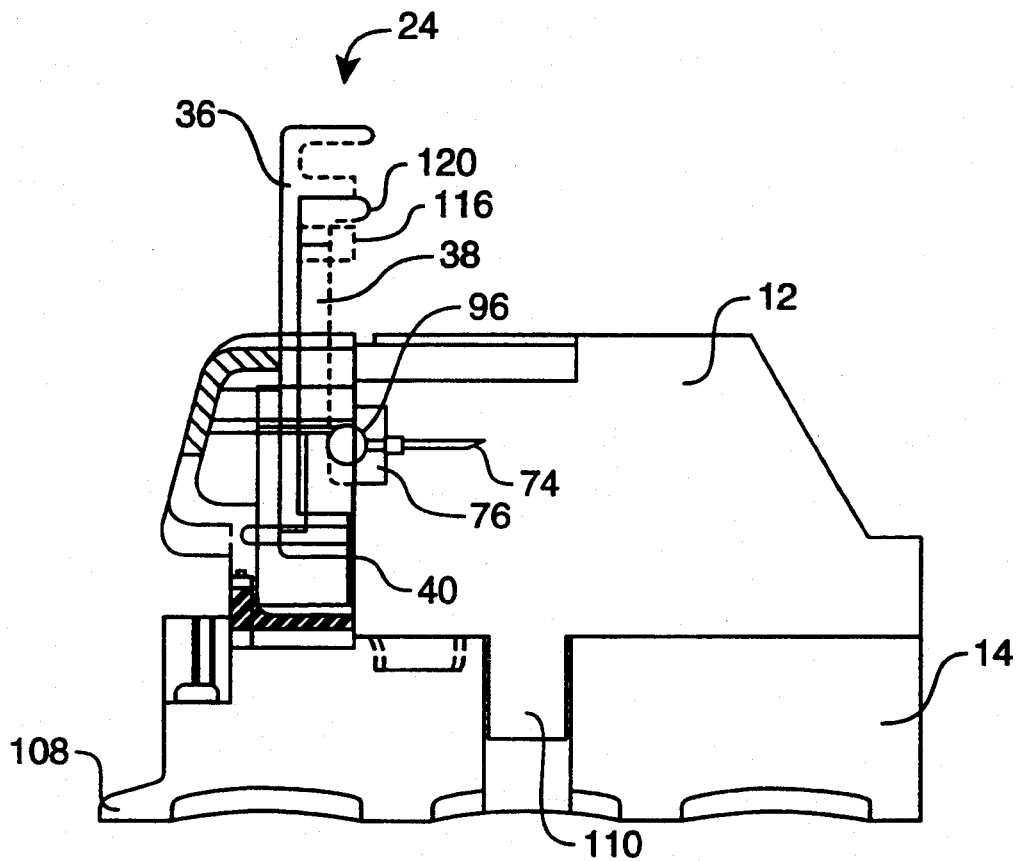
FIG. 7C is a front elevation of the device showing the sealing mechanism and cutting mechanism in phantom before the cutting apparatus has been engaged.

The device 10 includes a manifold 76 (shown in FIGS. 3 and 6A-6C) which adjoins the inner face 90 of the right wall 86 of the first housing 12 (see FIG. 3). The manifold 76 comprises a first face 82 (FIGS. 6A-6C) and a second face 83 (FIGS. 3 and 6B-6C). As shown in FIGS. 6A-6C, the manifold first face 82 includes a manifold aperture 80 which extends through to the manifold second face 83. The manifold second face 83 includes a ball valve seat 94. The manifold 76 is attached to the device 10 with the manifold aperture 80 positioned over the molded channel 92 (FIG. 5B) of the inner face 90 and the communicating holes 72 of the right wall 86 of the first housing 12. Thus, the manifold first face 82 adjoins the inner face 90 of the right wall 86.

The manifold 76 and right wall 86 communicate the vacuum available at the communicating holes 72 and molded channel 92 (provided from the blood collection tubes 64 via the needles 74, as explained above) into the manifold aperture 80. Furthermore, the manifold aperture 80 communicates the vacuum to a ball valve seat 94. A ball 96 placed into the valve seat 94 seals off the vacuum available at the valve seat 94 and manifold aperture 80 (FIGS. 3–4B and 6B).

As shown in FIGS. 1 and 3, the device 10 includes a plurality of barbs 98 molded to the inner surface 13 of the second housing 14 which hold an umbilical cord 16 in place on the device 10. In another preferred embodiment of the device 10, the barbs 98 are replaced with an abrasive surface (not shown) on the inner surface(s) 13 of either the first or second housings 12 and 14 or both. In all cases, the barbs 98 or the abrasive surface(s) securely hold the umbilical cord 16 in the housings 12 and 14 and help prevent its release. The inner surface 13 of the second housing 14 also includes a plurality of guide fingers 100 molded thereto which hold the cord 16 in proper alignment on the device 10 (FIGS. 1 and 3).

In addition, an upset anvil 102 is attached to the inner surface 13 of the second housing 14. The upset anvil 102 is made from a thin sheet of flexible material (an elastomer for example) and is held in place by a soft foam spring 104 (FIGS. 1 and 3). The upset anvil 102 is positioned on the inner surface 13 of the second housing 14 whereby the cutting edge 50 of the cutting apparatus 24 engages the upset anvil 102 as the cutting apparatus 24 passes through the slot 42 of the first housing 12 and into a cutting position for cutting the cord 16 (as in FIG. 2). The device 10 includes gels 106 which are attached to the inner surfaces 13 of the first and second housings 12 and 14 opposing each other (FIG. 3). The gels 106 are made of soft flexible conforming material (silicone gel for example) which conform to match and fit around the circumference of an umbilical cord 16 which is placed between them. The gel 106 of the second housing 14 is placed between the upset anvil 102 and the barbs 98 (see FIG. 3). The gel 106 of the first housing 12 meets the gel 106 of the second housing 14 when the device 10 is placed in a closed position.

The protector 28 is movably mounted on the first housing 12 (at the right side 86) and positioned directly below the sheath cap 62 when the blood collection apparatus 22 is mounted on the device 10 (FIG. 3). The sheath cap 62 limits the movement of the protector 28. When the blood collection apparatus 22 is removed from the device 10, an upset wall 128 on the sheath cap 62 forces the protector 28 to rotate to a position whereby the protector 28 clamps off the blood flow from the cord 16 and blocks the exposed ends of the needles 74 (the needles 74 are exposed due to the removal of the blood collection apparatus 22).

The manipulation and operation of the device 10 will now be described in detail. The device 10 is packaged in an open, ready to use, position whereby a physician (or other user) may grasp the device 10 with one hand. The device 10 includes two sets of detents (described above). One set is on the first and second housings 12 and 14 and the other is on the clamp 18. The detents hold the device 10 open to an angle of approximately sixty degrees and prevent premature accidental closing of the device 10. When the baby 20 is delivered the user will support the baby 20 with one hand while grasping the device 10 with the other. The device 10 is placed around the umbilical cord 16 with an alignment bumper 108 (FIGS. 1–3) molded on the left side 87 of the second housing 14 is positioned toward the baby 20 (FIG. 2). The alignment bumper 108 may be placed directly against the baby's stomach if desired, leaving a cord protrusion from the baby 20 of about a half inch. It is not necessary for the bumper 108 to touch the baby 20 and the device 10 may be placed anywhere along the umbilical cord 16 as long as the bumper 108 is positioned toward the baby 20 (FIG. 2). Once the device 10 is in position, the user closes the first and second housings 12 and 14 toward each other to thereby force a locking latch 110 which is molded on the front side 84 of the first housing 12 (FIGS. 1–3 and 5A–5B) onto a locking latch receiver 112 which is molded on the front side 84 of the second housing 14 (FIGS. 1 and 3) to thereby lock the device 10 in a closed position (FIG. 2).

When the device 10 is closed, the clamp 18 is also closed. As described above, the clamp 18 comprises a top arm 30 and a bottom arm 32 (FIGS. 1–3). As shown in FIGS. 1 and 3, the top arm 30 of the clamp 18 includes a clamp latch 114 and the bottom arm 32 includes a clamp latch receiver 115. When the device 10 is closed, the clamp latch 114 snaps into the clamp latch receiver 115 to thereby close the clamp 18 around the entrapped umbilical cord 16 whereby the cord 16 between the baby 20 and the device 10 collapses and the blood flow is clamped off (FIG. 2). Although the clamp 18 is closed, it is held in place on the device 10 by the rocker 52 which is supported by the floor 58 of the shelf slot 54 on the slide 36 (FIG. 3). Meanwhile, the gels 106 in the first and second housings 12 and 14, are forced over and around the circumference of the entrapped cord 16 to thereby form a seal around the entire periphery of the cord 16 (FIG. 3). The gels 106 must be made of soft and conforming material (e.g. silicone gel) to allow contact with all nooks and crannies of all varieties of umbilical cords 16 and to thereby create a leak proof seal around an entrapped umbilical cord 16 while not unduly clamping the cord 16 or constraining the blood flow within the cord 16.

Once the device 10 is closed, the user may engage the finger grip 46 with the thumb of the hand holding the device 10 and slide the safety lock 26 to thereby disengage the locking tip 44 from the lock notch 48 to thereby free the cutting apparatus 24 (FIG. 3). The user's same thumb may now depress the slide 36 of the cutting apparatus 24 forcing the cutting edge 50 of the blade 40 through the entrapped cord 16 and into the upset anvil 102 (FIG. 3). The upset anvil 102, upon reaching its buckling load, collapses against the light force of the soft foam spring 104 to thereby allow the cutting edge 50 to proceed toward the second housing 14 (FIG. 3). The upset anvil 102 is shown in FIG. 2 as it appears after the cutting action. This method of using a buckling upset anvil 102 allows the blade 40 to move through the cord 16 and into soft elastomer which buckles out of the way to thereby ensure a clean cut and allow a low cutting force.

While the blade 40 cuts through the cord 16 the shelf slot 54 of the slide 36 moves toward the second housing 14 (FIG. 3). The ceiling 56 of the shelf slot 54 engages the back foot 52 of the rocker 34 to thereby force the rocker 34 to rotate and push the clamp 18 out of the device 10 (FIG. 3). The rocker 34 is made of thin metal (preferably stainless steel) which is much harder than the top arm 30 of the clamp 18 (which is made of soft injection molded plastic). The advantage of this mechanism is to allow a physical dimension to be set in reference to the rocker 34 and the support of the bottom arm 32 of the clamp 18. Excess tolerance will be taken up by the rocker 34 penetrating into the top arm 30 of the clamp 18. The physical dimensional control assures that the clamp 18 will lock when the device 10 is closed regardless of the size of the entrapped umbilical cord 16. The size of a human umbilical cord 16 may vary from less than one third of an inch to slightly over an inch in diameter. Therefore, it is important to insure that a clamp 18 locks around a variety of different sizes of umbilical cords 16.

As described above, the cutting apparatus 24 includes a gasket 38 which is attached to the slide 36 (FIGS. 3 and 4A-4B). As shown in FIG. 4B, the gasket 38 includes a seal 120 which surrounds a gasket pocket 122 and a blood flow channel 124. FIGS. 7A-7C and 8A-8H show the sealing mechanism of the device 10 in conjunction with the cutting mechanism described above. As described above, the device 10 is used to entrap an umbilical cord 16 (FIGS. 8A-8B), sever the entrapped cord 16 (FIGS. 8C-8F), and clamp and eject one severed end of the cord 16 to thereby release the baby 20 (FIG. 2). The other severed end of the cord 16 comprises a cord opening 126 (FIGS. 7A-7B and 8E-8H) and is attached to the placenta (not shown). The device 10 collects blood samples from the cord opening 126 of the cord 16 (FIGS. 2, 7A-7B, and 8E-8H).

As shown in FIG. 4B, the cutting apparatus 24 includes an upset pin 116 which is molded to the slide 36 and protrudes out of an opening 118 in the gasket 38 when the cutting apparatus 24 is assembled. The upset pin 116 is an important feature of the device 10 with regard to collecting blood samples. As described above, the cutting apparatus 24 is manipulated to sever a cord 16 by forcing the cutting apparatus 24 downward into a cutting position (FIG. 2). As the cutting apparatus 24 moves downward, the upset pin 116 also moves downward toward the second housing 14 and contacts a ball 96 (seated in the ball valve seat 94 in the manifold 76) which is sealing off the vacuum from the blood collection tubes 64 (FIGS. 7A-7C and 8A-8H). The pin 116 contacts the ball 96 at the precise time that the seal 120 completely surrounds the cord opening 126 (FIGS. 7A-7C and 8A-8H). As the slide 36 is pushed to its furthest downward position, the upset pin 116 moves the ball 96 out from the ball valve seat 94 (FIG. 7B) to thereby allow communication of the vacuum from the blood collection tubes 64 through the needles 74, the communicating holes 72 in the first housing 12, the manifold 76 (via the manifold aperture 80), the ball valve seat 94, and the gasket pocket 122 and blood flow channel 124 in the gasket 38 to the just cut face of the cord 16 which defines the cord opening 126 (see FIGS. 8G-8H). The seal 120 is designed to enclose the cord opening 126 whereby the blood in the cord 16 moves directly into the blood collection tubes 64 (via the opened vacuum) as soon as the cord 16 is cut by the cutting edge 50 of the blade 40 (see FIGS. 8G-8H).

Figure 8A:
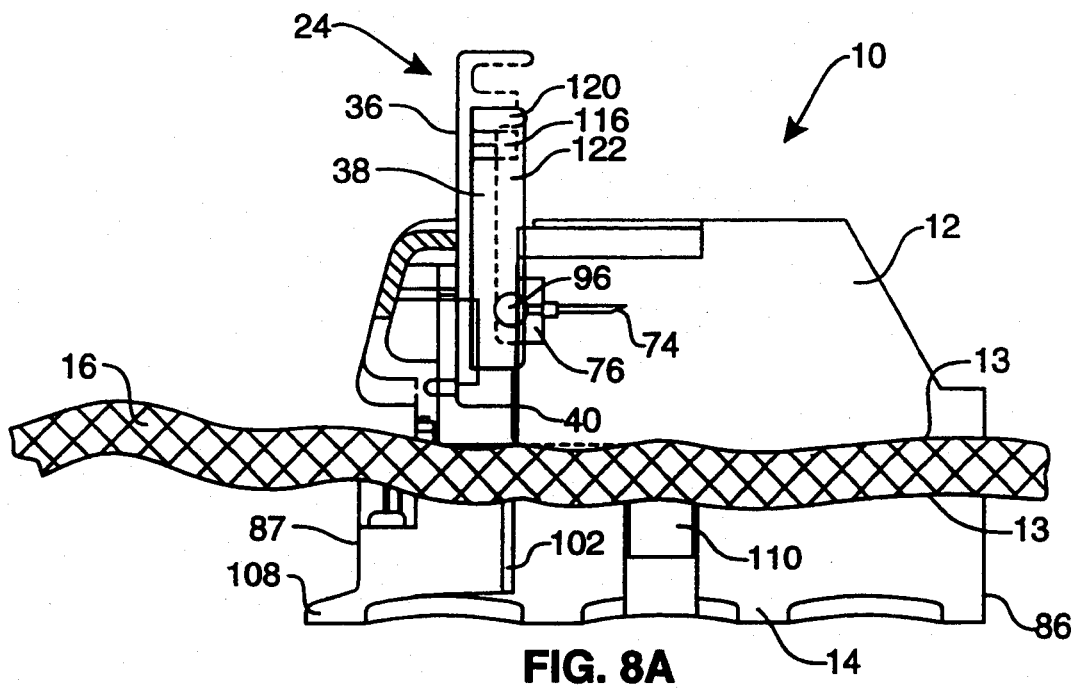
FIG. 8A is a front elevation of the device without the blood collection apparatus showing an umbilical cord enclosed in the device and various features of the device in phantom.
Figure 8B:
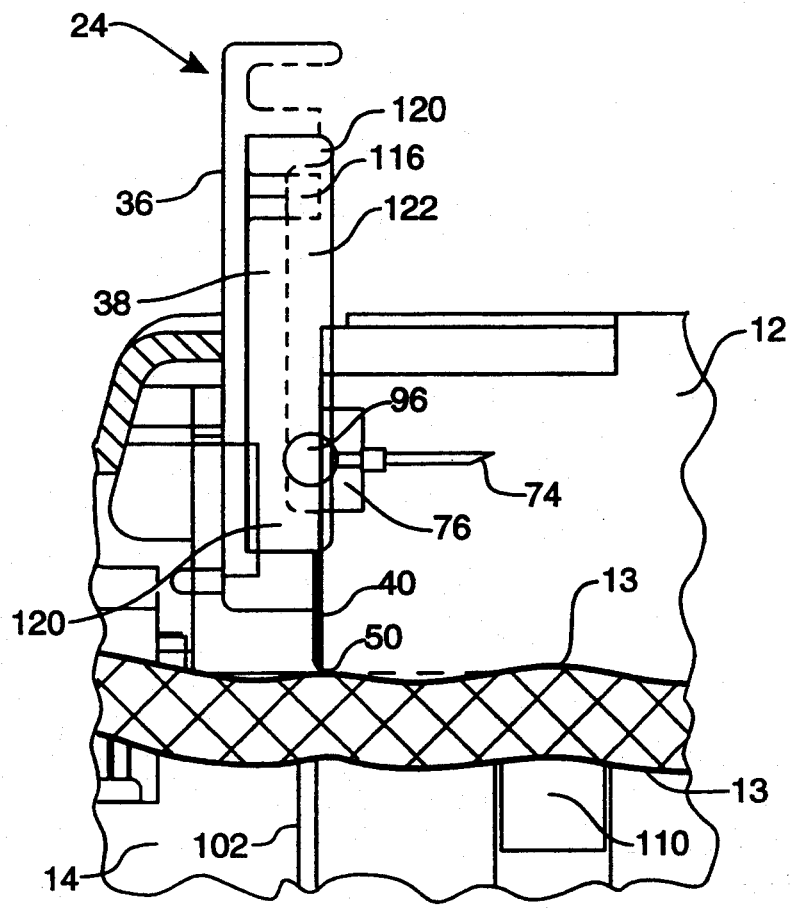
FIG. 8B is an enlarged view of a portion of the device of FIG. 8A.
Figure 8C:
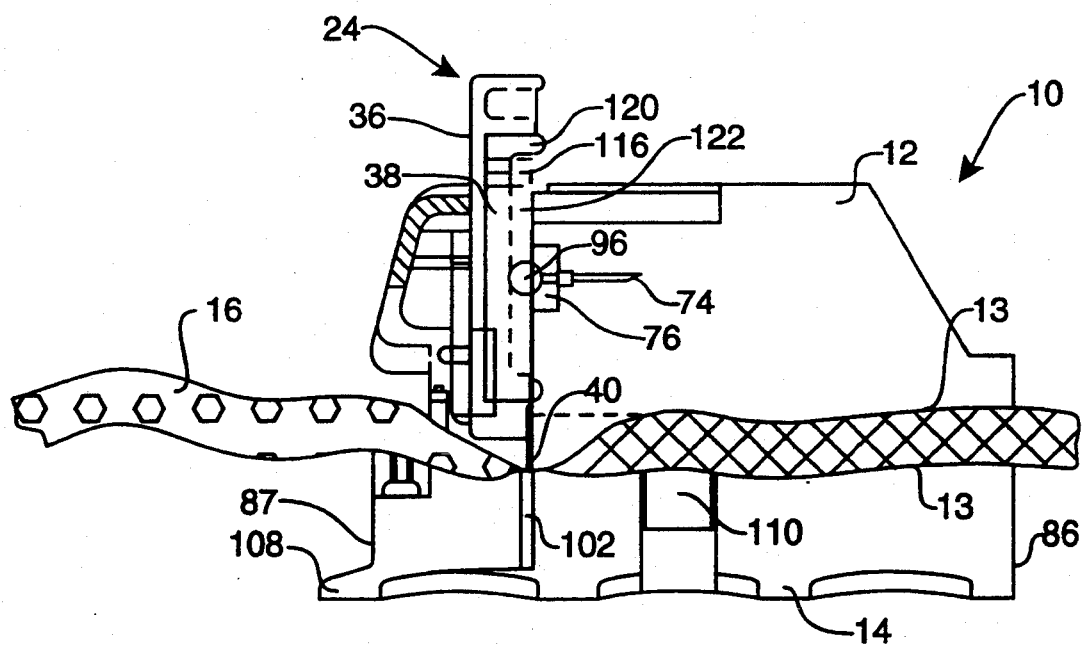
FIG. 8C is a front elevation of the device without the blood collection apparatus showing the dynamics of the cord cutting mechanism and various features of the device in phantom.
Figure 8D:
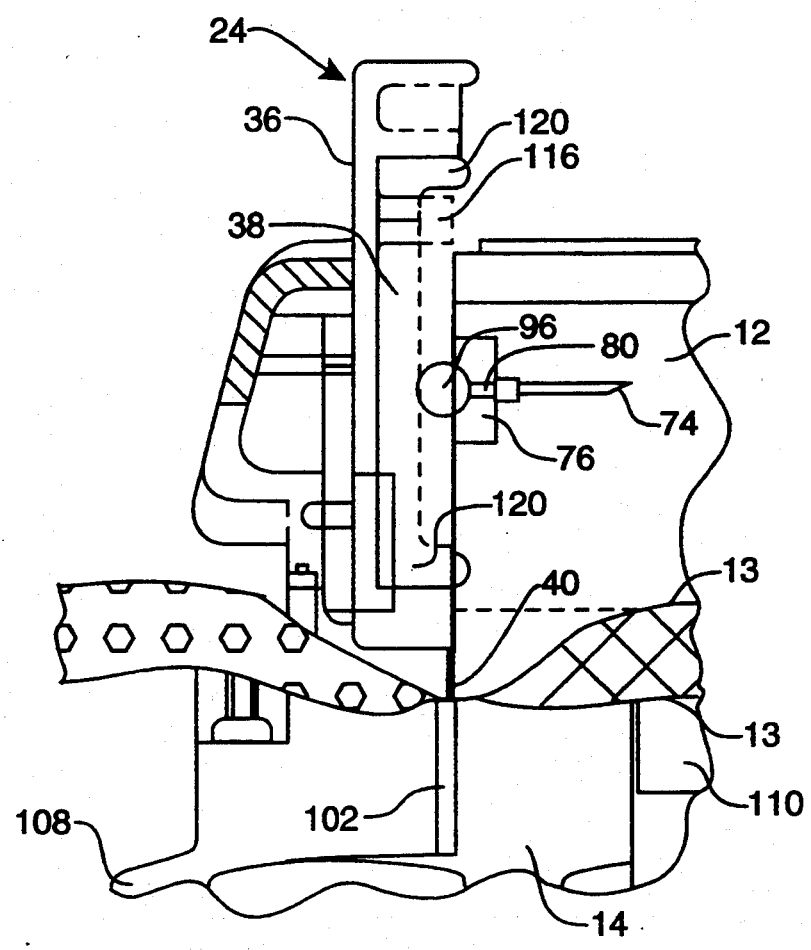
FIG. 8D is an enlarged view of a portion of the device of FIG. 8C.
Figure 8E:
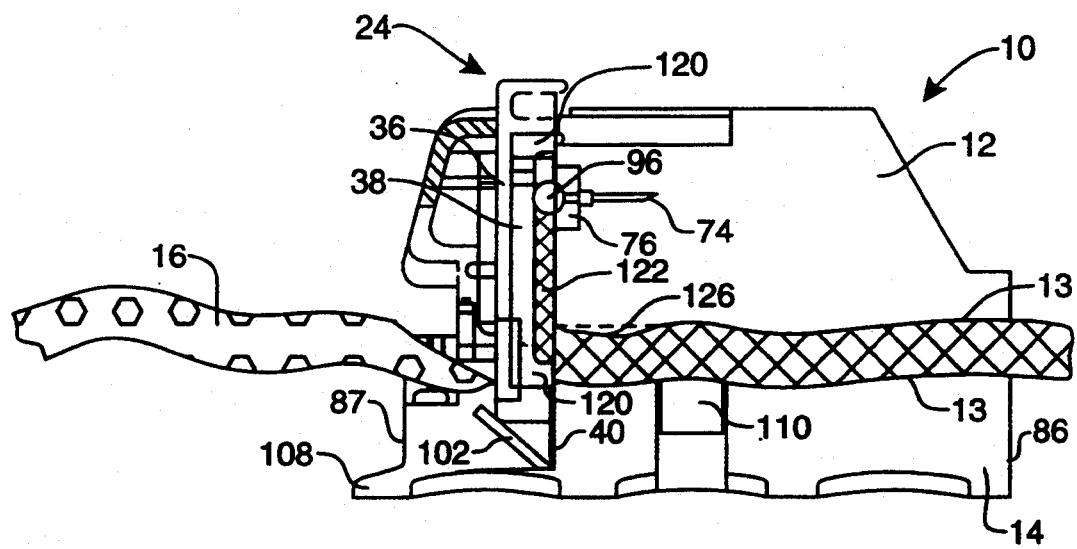
FIG. 8E is a front elevation of the device without the blood collection apparatus showing the dynamics of the cord cutting and blood collecting mechanisms and various features of the device in phantom.
Figure 8F:
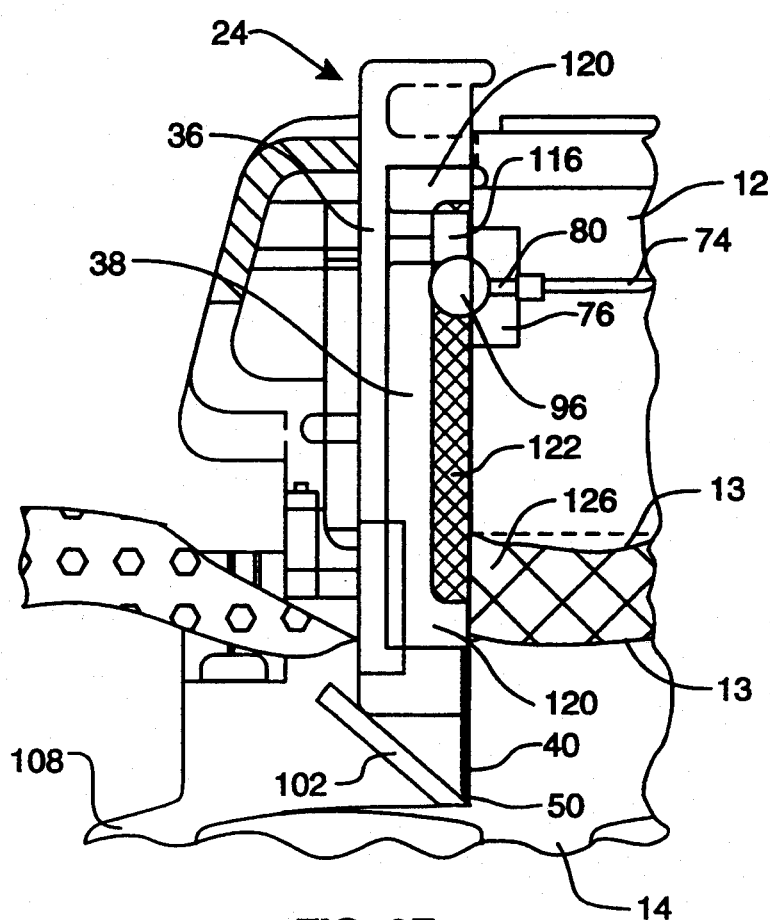
FIG. 8F is an enlarged view of a portion of the device of FIG. 8E.
Figure 8G:
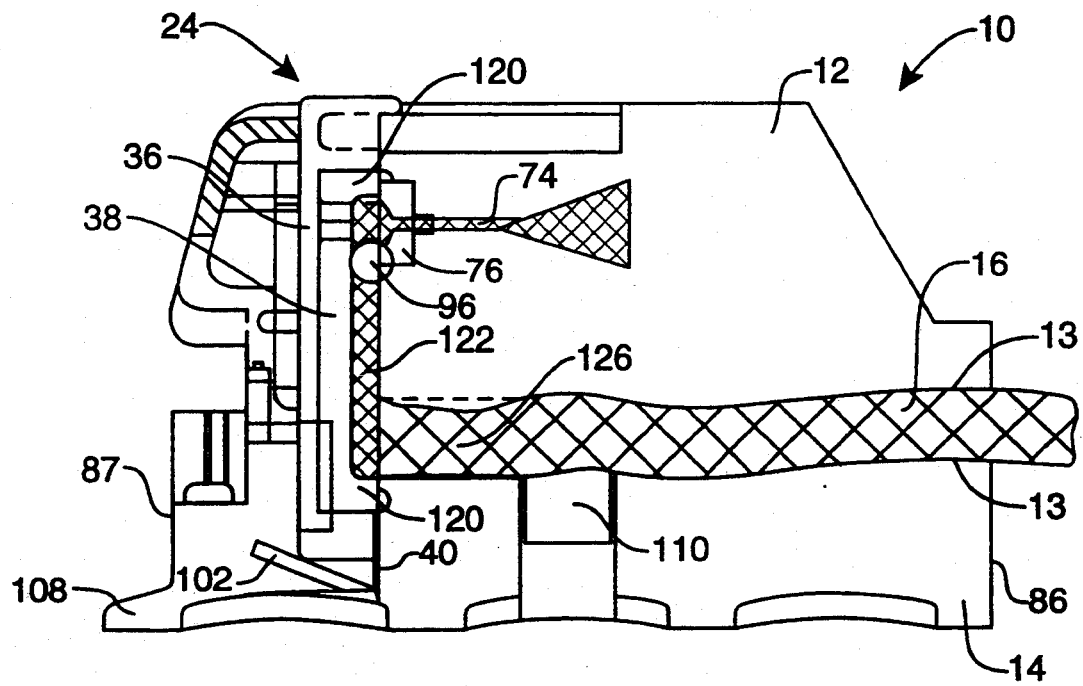
FIG. 8G is a front elevation of the device without the blood collection apparatus showing the dynamics of the blood collecting mechanism and various features of the device in phantom.
Figure 8H:
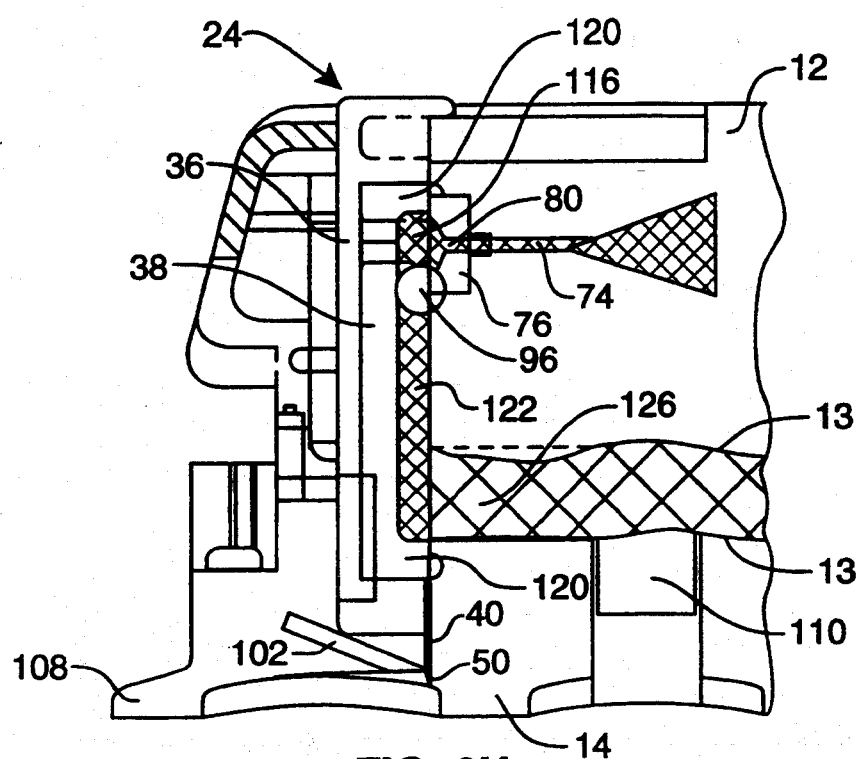
FIG. 8H is an enlarged view of a portion of the device of FIG. 8G.

FIGS. 8A-8H show the blood collection procedure in detail. FIGS. 8A and 8B show the device 10 (without the blood collection apparatus 22) after an umbilical cord 16 has been entrapped and the cutting apparatus 24 has been released and is in position to cut the cord 16. The ball 96 is positioned in the ball valve seat 94 (FIGS. 8A-8B) blocking off the vacuum from the blood collection apparatus 22 (not shown). FIGS. 8C and 8D show the device 10 (without the blood collection apparatus 22) as the blade 40 of the cutting apparatus 24 cuts through the entrapped cord 16 and meets the upset anvil 102. The ball 96 is still positioned in the ball valve seat 94 (FIGS. 8C-8D). FIGS. 8E and 8F show the device 10 (without the blood collection apparatus 22) after the blade 40 has initially cut through the cord 16 and the upset anvil 102 buckles out of the way. The seal 120 of the gasket 138 does not quite completely surround the cord opening 126 formed when the cord 16 was cut and the blood flowing in the cord 16 has entered and filled the gasket pocket 22 and blood flow channel 24 (FIGS. 8E-8F). The ball 96 is still positioned in the ball valve seat 94 (FIGS. 8E-8F). FIGS. 8G and 8H show the device 10 (without the blood collection apparatus 22) after the cutting apparatus 24 has been placed in a fully cut position, the upset anvil 102 is fully buckled, the seal 120 completely surrounds the cord opening 126, and the upset pin 116 of the slide 36 has dislodged the ball 96 to thereby expose the blood in the gasket pocket 122 and blood flow channel 124 to the vacuum available at the manifold aperture 80 from the blood collection tubes 64 (not shown). The vacuum from the blood collection tubes 64 draws the blood through the manifold aperture 80, the communicating holes 72 in the first housing 12, the needles 74 and into the tubes 64 (not shown).

Once the blood collection tubes 64 have been filled with cord 16 blood, the blood collection apparatus 22 may be removed from the device 10 by merely pulling the apparatus 22 outward from the device 10 (FIG. 3). As the blood collection apparatus 22 is pulled from the device 10, an upset wall 128 molded to the sheath cap 62 (which is removed with the blood collection apparatus 22) engages an escapement 130 molded on the protector 28 to thereby force the protector 28 to rotate (clockwise in FIG. 3). As the protector 28 rotates, needle notches 132 (FIG. 3) are snapped past and block the needles 74. Furthermore, a cord squeezer wall 134 (FIG. 3) is rotated against and clamps off the cord 16 which is still attached to the placenta to thereby clamp off any blood flow from the placenta. The pressure of the cord 16 on the cord squeezer wall 134 stops clockwise movement of the protector 28 while pressure of the needles 74 against the protector 28 prevents counterclockwise movement (FIG. 3). This positioning of the protector 28 clamps the cord 16 to thereby prevent further blood flow from the placenta (not shown) while also protecting medical personnel from puncture wounds by blocking the needles 74.

The blood collection tubes 64 can be easily extracted from the protective sheath 60 by a simple two step process: (1) the sheath cap 62 is squeezed to thereby unlock the sheath cap 62 from the protective sheath 60 and expose the blood collection tubes 64, and (2) the blood collection tubes 64 are removed from the protective sheath 60 (FIG. 3). The outside of the tubes 64 are free of contamination from blood flow exposure during the procedure which allows personnel to easily label each tube 64 with information (such as patient identification). Two blood collection tubes 64 are preferably used so one may be pre-loaded with the precise amount of anticoagulant needed for testing the blood sample (FIG. 3). Other devices can be easily manufactured using different numbers and/or types of blood collection tubes 64 which are filled with varying amounts and types of chemicals.

The present device 10 can also include, for little extra cost, a through hole 200 on the left side 86 of the device 10 (see FIGS. 1–3 and 9), a similar matching through hole 210 on the slide 36 (see FIGS. 3–4B), and a thin wall 220 molded into the gasket 38 (see FIGS. 3–4B). These features enable certain on-the-spot analyses to be performed.

After the device has been clamped over an umbilical cord, and the cord has been cut and blood sampled, a small volume of blood is left in the slot 124 of the gasket 38. The blood left in the slot 124 makes direct communication with a thin wall 220 molded into the gasket 38 and located directly behind the through hole 210 in the slide 36 (see FIGS. 3–4B). A probe (not shown) containing any of a number of electrode or optical sensors can be placed through the holes 200 and 210 to make direct contact with the thin wall 220 which is wet on its other side with blood in the slot 124. The probe may thereby make a measurement of the blood. For example, blood pH measurements are commonly made by placing a Clark electrode directly onto a thin wall membrane which separates the blood to be tested from the sensor. Similarly, saturated oxygen measurements may be made by directing infra-red light emitted by a probe through the thin wall 220 and measuring reflected light. Thus, the additional features of through holes 200 and 210 and thin wall membrane 220 enable on-the-spot measurements of non-contaminated blood immediately at birth.

While a preferred embodiment of the present invention has been shown and described, various modifications may be made without departing from the scope of the present invention, and all such modifications and equivalents are intended to be covered.

What is claimed is:

1. Apparatus for cutting an umbilical cord and collecting a blood sample therefrom, comprising:
   a housing enabling receiving and entrapping a portion of umbilical cord, a hole in the housing enabling access to a thin wall membrane which is in contact with blood from the umbilical cord; and
   a cutter movably attached to said housing enabling cutting an umbilical cord and directing blood contained within the umbilical cord to a blood receiver;
   said housing holding said blood receiver and enabling fluid communication between the blood within the umbilical cord and the blood receiver whereby the blood receiver receives blood contained in the umbilical cord in a clean manner.

2. Apparatus for cutting an umbilical cord and collecting a blood sample therefrom, comprising:
   a housing enabling receiving and entrapping a portion of umbilical cord;
   a cutter movably attached to said housing enabling cutting an umbilical cord and directing blood contained within the umbilical cord to a blood receiver;
   a shelf member on the cutter; and
   a clamp removably attached to the housing by means of a rocker and closable around the umbilical cord to collapse the cord and occlude blood flow therethrough, the rocker rotatably attached to said housing and having a first foot and a second foot, said first foot for engaging and holding the clamp on the housing, said second foot for engaging the shelf of the cutter whereby the shelf rotates the rocker thereby ejecting the clamp from the housing while maintaining the clamp on the umbilical cord when the cutter moves to enable cutting of the umbilical cord;
   said housing holding said blood receiver and enabling fluid communication between the blood within the umbilical cord and the blood receiver whereby the blood receiver receives blood contained in the umbilical cord in a clean manner.

3. Apparatus for cutting an umbilical cord and collecting a blood sample therefrom, comprising:
   a housing enabling receiving and entrapping a portion of umbilical cord, the housing including at least one communicating hole;
   a cutter movably attached to said housing enabling cutting an umbilical cord and directing blood contained within the umbilical cord to a blood receiver, the cutter including an upset pin for unseating an obstructor, the blood receiver removably attached to the housing and containing a vacuum which is exposed when the obstructor is unseated, the vacuum enabling collection of blood from the umbilical cord through the communicating hole in the housing;
   said housing holding said blood receiver and enabling fluid communication between the blood within. She umbilical cord and the blood receiver whereby the blood receiver receives blood contained in the umbilical cord in a clean manner.

4. The apparatus of claim 3 further comprising at least one needle mounted in the communicating hole in the housing and mounted to the blood receiver to thereby provide communication of the vacuum within the blood receiver to the communicating hole in the housing, and
   a protector movably attached to the housing for covering the at least one needle which is exposed when the blood receiver is removed from the housing.

5. An umbilical cord clamping and cutting device comprising
   a first housing and second housing movably connected together and movable to a closed position to entrap at least a portion of an umbilical cord,
   a cutter attached to the first housing and movable from a disengaged position to an engaged position to thereby cut an entrapped umbilical cord,
   a clamp attached to the first housing and closable around an umbilical cord to collapse the cord and occlude blood flow therethrough when the first housing and second housing are moved to a closed position, and
   means interconnecting said cutting member and said clamp for releasing the clamp and a severed umbilical cord end from the first housing and second housing when the cutting member is moved to an engaged position.

6. The device of claim 5 further comprising
   a hole in the first housing enabling access to a thin wall membrane which is in contact with blood from the umbilical cord.

7. An umbilical cord clamping and cutting device comprising:
   a first housing and second housing movably connected together and movable to a closed ..position to entrap at least a portion of an umbilical cord;
   a cutter attached to the first housing and movable from a disengaged position to an engaged position to thereby cut an entrapped umbilical cord;
   an anvil attached to the second housing to encounter the cutter when said cutter is moved to an engaged position;

a first gel on the first housing and a second gel on the second housing for circumscribing the entrapped umbilical cord and thereby forming a seal around the cord and between the cord and the first housing and second housing; and a blood collector removably attached to the first housing for collecting blood from the umbilical cord, the blood collector including a vacuum and a valved mechanism which is movable from a closed position to an open position thereby enabling blood from the cord to be exposed to the vacuum and collected in the collector.

* * * * *